(12) United States Patent
Yamagata

(10) Patent No.: US 8,754,235 B2
(45) Date of Patent: Jun. 17, 2014

(54) METHOD FOR PRODUCING 5-(AMINOMETHYL)-2-CHLOROTHIAZOLE

(75) Inventor: Kazuyuki Yamagata, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 171 days.

(21) Appl. No.: 13/508,952

(22) PCT Filed: Nov. 29, 2010

(86) PCT No.: PCT/JP2010/071766
§ 371 (c)(1),
(2), (4) Date: May 9, 2012

(87) PCT Pub. No.: WO2011/065590
PCT Pub. Date: Jun. 3, 2011

(65) Prior Publication Data
US 2012/0226049 A1 Sep. 6, 2012

(30) Foreign Application Priority Data
Nov. 30, 2009 (JP) ................................ 2009-271482

(51) Int. Cl.
*C07D 277/32* (2006.01)
(52) U.S. Cl.
USPC ....................................................... 548/202
(58) Field of Classification Search
USPC ....................................................... 548/202
See application file for complete search history.

(56) References Cited

U.S. PATENT DOCUMENTS

| | | | |
|---|---|---|---|
| 3,644,634 A | 2/1972 | Weyer et al. | |
| 4,720,558 A | 1/1988 | Kaulen | |
| 5,180,833 A | 1/1993 | Uneme et al. | |
| 6,008,363 A | 12/1999 | Uneme et al. | |
| 6,251,625 B1 | 6/2001 | Bommarius et al. | |

FOREIGN PATENT DOCUMENTS

| | | |
|---|---|---|
| EP | 1024133 A2 | 8/2000 |
| GB | 850982 | 10/1960 |
| JP | 59-122444 A | 7/1984 |
| JP | 3-223252 A | 10/1991 |
| JP | 4-21674 A | 1/1992 |
| JP | 4-234864 A | 8/1992 |
| JP | 5-286936 A | 11/1993 |
| JP | 10-120666 A | 5/1998 |
| WO | WO 97/00867 A1 | 1/1997 |
| WO | WO 97/03091 A1 | 1/1997 |
| WO | WO 97/33809 A1 | 9/1997 |

OTHER PUBLICATIONS

International Preliminary Report on Patentability and Written Opinion of the International Searching Authority dated Jul. 19, 2012, for Application No. PCT/JP2010/071766.
Collet et al., "Solid Phase Decarbamoylation of Monoalkylureas and N-Carbamoylpeptides Using Gaseous NOx : A New Easy Deprotection Reaction With Minimum Waste", Tetrahedron Letters, vol. 40, 1999, p. 3355-3358.
Ford et al., "Unique and Common Metabolites of Thiamethoxam, Clothianidin, and Dinotefuran in Mice", Chem. Res. Toxicol., vol. 19, No. 11, 2006, p. 1549-1556.
International Search Report dated Feb. 22, 2011, for Application No. PCT/JP2010/071766.
Takahashi et al., "Microbial Transformation of Hydantoins to N-Carbamyl-D-Amino Acids", J. Ferment. Techno., vol. 57, No. 4, 1979, p. 328-332.
Yokota et al., "Absorption, Tissue Distribution, Excretion, and Metabolism of Clothianidin in Rats", J. Agric. Food Chem., vol. 51, No. 24, 2003, p. 7066-7072.
Badalova et al., "Reaction of 1-Amino-3-propoxy-2-propanol with Aldehydes," Russian Journal of Applied Chemistry, vol. 78, No. 10, 2005, pp. 1656-1658.
Brown et al., "Pyrimidine Metabolism and Secondary Product Formation: Biogenesis of Albizziine, 4-Hydroxyhomoarginine and 2,3-Diaminopropanoic Acid," Phytochemistry, vol. 40, No. 3, 1995, pp. 763-771.
Database CA (online) retrieved from STN, Database accession No. 1984:631030 & JP59122444.
Kennedy et al., "Mechanism of Reaction of Cyanogen Bromide-Activated Agarose with Amines and the Solvolysis of Amine Ligands," The British Polymer Journal, vol. 15, No. 3, Sep. 1983, pp. 133-138.
Sidorov et al., "Solid-Phase Catalytic Hydrogenation of Uracil with Tritium: Synthesis of Tritium-Labeled Beta-Alanine," Radiochemistry, vol. 44, No. 3, 2002, pp. 295-297.
Tordini et al., "Theoretical Study of Hydration of Cyanamide and Carbodiimide," J. Phys. Chem. A., vol. 107, 2003, pp. 1188-1196.
Yokozeki et al., "Mechanism of Asymmetric Production of L-Aromatic Amino Acids from the Corresponding Hydantoins by Flavobacterium," Agricultural & Biological Chemistry, vol. 51, No. 3, 1987, pp. 737-746.

*Primary Examiner* — Shawquia Young
(74) *Attorney, Agent, or Firm* — Birch, Stewart, Kolasch & Birch, LLP

(57) ABSTRACT

A method for producing 5-(aminomethyl)-2-chlorothiazole, which comprises the step of mixing a compound represented by formula (2):

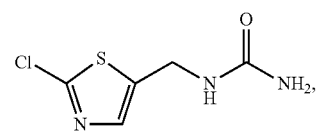

(2)

a mineral acid and a nitrite salt together.

8 Claims, No Drawings

METHOD FOR PRODUCING 5-(AMINOMETHYL)-2-CHLOROTHIAZOLE

TECHNICAL FIELD

The present invention relates to a method for producing 5-(aminomethyl)-2-chlorothiazole.

BACKGROUND ART 5-(Aminomethyl)-2-chlorothiazole is used as an intermediate for the synthesis of pharmaceuticals, agricultural chemicals and the like. JP-A-04-234864 describes, as a method for its production, a method in which an allyl isothiocyanate derivative is reacted with a chlorinating agent and then the obtained product is reacted with liquid ammonia or hexamethylenetetramine.

DISCLOSURE OF THE INVENTION

The present application relates to the following inventions.

[1] A method for producing 5-(aminomethyl)-2-chlorothiazole, which comprises the step of mixing a compound represented by formula (2):

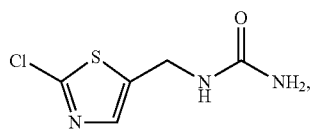

(2)

a mineral acid and a nitrite salt together.

[2] The method according to [1], wherein the mineral acid is at least one selected from the group consisting of hydrochloric acid, sulfuric acid and phosphoric acid.

[3] A method for producing a compound represented by formula (2):

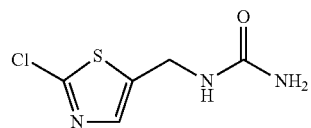

(2)

which comprises the step of hydrolyzing a compound represented by formula (1):

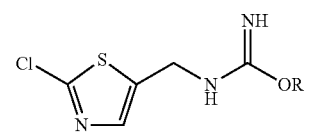

(1)

wherein R represents a linear alkyl group having 1 to 6 carbon atoms or a cyclic alkyl group having 3 to 6 carbon atoms, and each of the linear alkyl group and the cyclic alkyl group may have a substituent.

[4] A method for producing 5-(aminomethyl)-2-chlorothiazole, which comprises the steps of:

hydrolyzing a compound represented by formula (1):

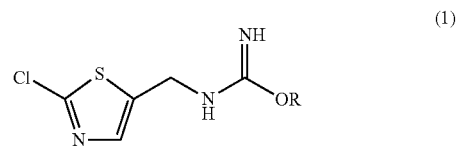

(1)

wherein R represents a linear alkyl group having 1 to 6 carbon atoms or a cyclic alkyl group having 3 to 6 carbon atoms, and each of the linear alkyl group and the cyclic alkyl group may have a substituent, and mixing a compound obtained in the above step and represented by formula (2):

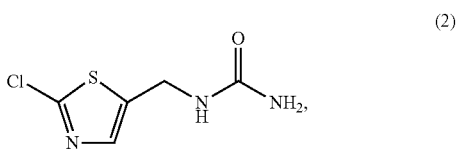 [SMILES: NC(=O)NCc1cnc(Cl)s1]

(2)

a mineral acid and a nitrite salt together.

[5] The method according to [4], wherein the mineral acid is at least one selected from the group consisting of hydrochloric acid, sulfuric acid and phosphoric acid.

[6] The method according to [4], wherein the compound represented by formula (1) is a compound contained in a solution obtained by mixing 5-(aminomethyl)-2-chlorothiazole with a compound represented by formula (3):

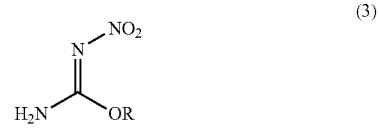

(3)

wherein R has the same meaning as defined in [4], in the presence of a solvent to obtain a mixture containing a compound represented by formula (4):

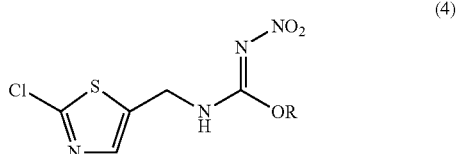

(4)

wherein R has the same meaning as defined above, and the compound represented by formula (1), and then subjecting the mixture to solid-liquid separation.

[7] The method according to [6], wherein the solvent is water or a mixed solvent of water and an organic solvent.

[8] A method for producing a compound represented by formula (4):

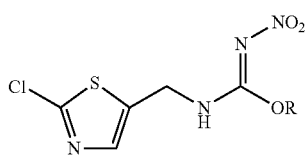

(4)

wherein R is as defined in [4], which comprises the step of mixing 5-(aminomethyl)-2-chlorothiazole obtained by the method according to [4] with a compound represented by formula (3):

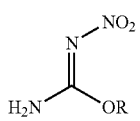

(3)

wherein R has the same meaning as defined above.

MODE FOR CARRYING OUT THE INVENTION

The present invention will be described in detail below.

The method for producing 5-(aminomethyl)-2-chlorothiazole of the present invention comprises the step of mixing a compound represented by formula (2) (hereinafter, this compound is sometimes referred to as compound (2)):

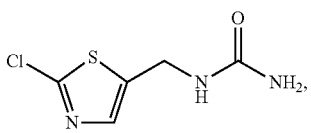

(2)

a mineral acid and a nitrite salt together (hereinafter, the present step is sometimes referred to as "decarbamoylation step").

Examples of the mineral acid include hydrochloric acid, sulfuric acid, and phosphoric acid, and sulfuric acid is preferable.

The mineral acid may be used after being diluted with water. When diluted with water, the concentration of the mineral acid is usually within a range of from 5 to 35% by weight.

The amount of the mineral acid is usually within a range of from 2 to 8 mol, and preferably from 4 to 6 mol, based on 1 mol of the compound (2).

Examples of the nitrite salt include alkali metal salts of nitrous acid, such as sodium nitrite and potassium nitrite; and alkaline earth metal salts, such as calcium nitrite, and alkali metal salts of nitrous acid are preferable and sodium nitrite is more preferable.

The amount of the nitrite salt is usually within a range of from 1 to 3 mol, and preferably from 1.1 to 1.5 mol, based on 1 mol of the compound (2).

There is no particular limitation on the mixing order of the compound (2), a mineral acid and a nitrite salt. The compound (2) may be mixed with a mineral acid and a nitrite salt, or a mineral acid and the compound (2) may be mixed with a nitrite salt, or a nitrite salt and the compound (2) may be mixed with a mineral acid. Preferably, a mineral acid is mixed with the compound (2), and the obtained mixture is mixed with a nitrite salt.

The mixing may be carried out in a solvent. There is no particular limitation on such a solvent and water is preferable.

The temperature in the decarbamoylation step is usually within a range of from 0 to 100° C., and preferably from 20 to 60° C.

The time of the decarbamoylation step is usually within a range of from 10 minutes to 48 hours, and preferably from 30 minutes to 6 hours.

In the reaction mixture (reaction solution, etc.) obtained in the decarbamoylation step, 5-(aminomethyl)-2-chlorothiazole is usually in the form of a mineral acid salt. Therefore, it is preferred to neutralize the reaction mixture with a base, such as sodium hydroxide or potassium hydroxide. The amount of the base in the neutralization is usually from 1 mol to 5 mol based on 1 mol of the mineral acid salt of 5-(aminomethyl)-2-chlorothiazole. The neutralization is carried out by mixing the reaction mixture with a base.

By the neutralization of the reaction mixture, a mixture (aqueous solution, etc.) containing 5-(aminomethyl)-2-chlorothiazole is obtained. The obtained mixture may be further subjected to a conventional post-treatment, such as extraction and washing with water, and may be subjected to a purification treatment, such as crystallization, extraction, distillation, adsorption using activated carbon, silica or alumina, and chromatography, such as silica gel column chromatography. The mixture may be recrystallized in the form of a mineral acid salt of 5-(aminomethyl)-2-chlorothiazole by adding the mineral acid.

The compound (2) can be obtained, for example, by hydrolyzing a compound represented by formula (1) (hereinafter sometimes referred to as compound (1)):

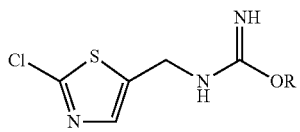

(1)

wherein R represents a linear alkyl group having 1 to 6 carbon atoms or a cyclic alkyl group having 3 to 6 carbon atoms, and each of the linear alkyl group and the cyclic alkyl group may have a substituent. A method for producing the compound (2) comprising the step of hydrolyzing the compound (1) also includes one of the present inventions.

As mentioned above, the compound (1) is a compound represented by formula (1).

Examples of R in formula (1) include linear alkyl groups having 1 to 6 carbon atoms, such as a methyl group, an ethyl group, a n-propyl group, a n-butyl group, an isopropyl group and a t-butyl group; and cyclic alkyl groups having 3 to 6 carbon atoms, such as a cyclopentyl group and a cyclohexyl group.

Each of the linear alkyl group and the cyclic alkyl group may have a substituent. Examples of the substituent include a halogen atom, and an alkoxy group having 1 to 4 carbon atoms.

Examples of the alkyl group having a substituent include haloalkyl groups such as a fluoromethyl group, a chloromethyl group, a trifluoromethyl group and a trichloromethyl group; (C1-C4 alkoxy) C1-C4 alkyl groups such as a methoxymethyl group and an ethoxyethyl group; haloalkyl groups such as a fluorocyclopentyl group and a chlorocyclopentyl group; and (C1-C4 alkoxy) C3-C6 cycloalkyl groups such as a methoxycyclopentyl group and an ethoxycyclopentyl group. Herein, "C1-C4" means that the number of carbon atoms is from 1 to 4, and "C3-C6" means that the number of carbon atoms is from 3 to 6.

R is preferably a linear alkyl group having 1 to 6 carbon atoms, more preferably a linear alkyl group having 1 to 4 carbon atoms, and still more preferably a methyl group and an ethyl group.

Specific examples of the compound (1) include N-[2-chlorothiazol-5-ylmethyl]-O-methyl-isourea, N-[2-chlorothiazol-5-ylmethyl]-O-ethyl-isourea, N-[2-chlorothiazol-5-ylmethyl]-O-propyl-isourea, and N-[2-chlorothiazol-5-ylmethyl]-O-butyl-isourea.

Usually, the hydrolysis of the compound (1) is carried out by bringing the compound (1) into contact with water in the presence of an acid or a base, and preferably in the presence of a base.

Examples of the acid include hydrochloric acid, sulfuric acid, and nitric acid. The amount of the acid is usually within a range of from 1 to 10 mol, and preferably from 2 to 6 mol, based on 1 mol of the compound (1).

Examples of the base include alkali metal hydroxides such as sodium hydroxide and potassium hydroxide. The amount of the base is usually within a range of from 1 to 10 mol, and preferably from 2 to 6 mol, based on 1 mol of the compound (1).

The amount of water is usually from 5 to 100 parts by weight, and preferably from 10 to 80 parts by weight, based on 1 part by weight of the compound (1).

Usually, the contact of the compound (1) with water is carried out by mixing the compound (1) with water.

The hydrolysis can be usually carried out at a temperature within a range of from 5 to 100° C., preferably from 20 to 90° C., and more preferably from 40 to 90° C. There is no particular limitation on the time of the hydrolysis, and the time may be usually from 1 to 24 hours.

Usually, the compound (2) obtained by the hydrolysis can be recovered as a crystal. The crystal of the compound (2) can be efficiently precipitated by cooling a reaction solution obtained by the hydrolysis to a temperature of −10 to 40° C. Recovery of the crystal can be carried out by a known method such as filtration and drying.

After the hydrolysis and before the precipitation of the crystal of the compound (2), the by-produced insoluble components are preferably removed. Removal of the insoluble components can be carried out by such a method as filtration and extraction with an organic solvent. When the insoluble components are removed by filtration, a filter aid such as diatomaceous earth is preferably used. Herein, the filter aid may have been added in case of carrying out the hydrolysis.

The compound (1) can be obtained as a by-product during an operation in which 5-(aminomethyl)-2-chlorothiazole is mixed with a compound represented by formula (3) (hereinafter sometimes referred to as compound (3)):

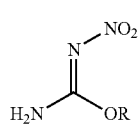

wherein R has the same meaning as defined above, to obtain a compound represented by formula (4) and useful as an intermediate for the production of a pesticide (hereinafter sometimes referred to as compound (4)):

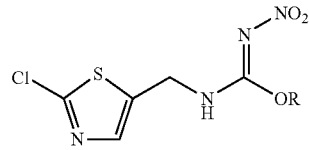

wherein R is as defined above.

In the operation for obtaining the compound (4), the compound (1) can be recovered as a solution by solid-liquid separation of a mixture obtained by mixing 5-(aminomethyl)-2-chlorothiazole with the compound (3). In this operation, 5-(aminomethyl)-2-chlorothiazole may be 5-(aminomethyl)-2-chlorothiazole obtained by the production method of the present invention.

The operation for obtaining the compound (4) is described in detail in JP-A-10-120666. Mixing of 5-(aminomethyl)-2-chlorothiazole with the compound (3) can be carried out usually in the presence of a solvent, for example, water or a mixed solvent of water and an organic solvent, and is preferably carried out in water. Examples of the organic solvent include aromatic hydrocarbons, such as benzene, toluene and xylene; halogenated hydrocarbons, such as dichloromethane, chloroform, 1,2-dichloroethane and carbon tetrachloride; saturated hydrocarbons, such as hexane, heptane and cyclohexane; ethers, such as diethyl ether, tetrahydrofuran and dioxane; ketones, such as acetone and methyl ethyl ketone; nitriles, such as acetonitrile and propionitrile; sulfoxides, such as dimethyl sulfoxide; acid amides, such as N,N'-dimethylformamide and N,N'-dimethylacetamide; esters, such as ethyl acetate and butyl acetate; and alcohols, such as methanol, ethanol, propanol and isopropanol. The mixing of 5-(aminomethyl)-2-chlorothiazole with the compound (3) is preferably carried out after dissolving the compound (3) in water. In this operation, the compound (4) is usually obtained as a crystal.

Since the reaction proceeds efficiently, the mixing is preferably carried out under the condition of pH 5 to 8, and more preferably of pH 6 to 7.5. The mixing is preferably carried out at a temperature of −10 to 50° C., and more preferably about 10 to 35° C.

More preferably, the mixing of 5-(aminomethyl)-2-chlorothiazole with a compound represented by formula (3) is carried out in water or a mixed solvent of water and an organic solvent under the conditions of pH 5 to 8. Solid-liquid separation can be carried out by such a known technique as filtration, sedimentation separation and decantation, and there is no particular limitation on the technique. The sedimentation separation can be carried out by gravity-type separation, centrifugation-type separation and the like. Examples of the filtration technique include gravity-type, vacuum-type, pressure-type and centrifugation-type techniques. The filtration may be carried out in a batch-wise manner or a continuous manner.

There is no particular limitation on the temperature and pH in the solid-liquid separation, and the separation may be carried out under the same conditions as those in the mixing, i.e., at −10 to 50° C. and at pH 5 to 8.

When the solid-liquid separation is carried out by filtration, not only a filtrate but also a solution, obtained in case of washing a crystal of the compound (4) obtained as a filtrated product, can be recovered as a solution containing the compound (1).

The compound (1) may be either a solution per se obtained by the solid-liquid separation, or a compound recovered from the solution by concentration and purification using a known method.

One example of the operation for obtaining the compound (4) includes a method in which the compound (3) is dissolved in water and 5-(aminomethyl)-2-chlorothiazole is mixed with the obtained solution at a temperature of about 10° C. to 35° C. to obtain a mixture containing the compound (4) and the compound (1), and then the mixture is subjected to solid-liquid separation to extract the compound (4) as a crystal. The solution obtained after extracting the compound (4) can be obtained as a solution containing the compound (1). Examples of the solution containing the compound (1) include a filtrate; and a supernatant obtained by sedimentation separation, decantation or the like.

The present inventor has found, as a method effectively utilizing the compound (1), a method for producing 5-(aminomethyl)-2-chlorothiazole, which comprises the step of hydrolyzing the compound (1) and the step of mixing the compound (2) obtained in the previous step, a mineral acid and a nitrite salt together.

In such a method for producing 5-(aminomethyl)-2-chlorothiazole, an embodiment, in which the compound (1) is a compound contained in a solution obtained by mixing 5-(aminomethyl)-2-chlorothiazole with the compound (3) in the presence of a solvent to obtain a mixture containing the compound (4) and the compound (1) and then subjecting the mixture to solid-liquid separation, is also provided as one of exemple of preferred embodiments.

Herein, the compound (3) can be obtained, for example, by nitration of an O-alkylisourea having an alkyl group of 1 to 6 carbon atoms. The nitration can be carried out by a method in which the O-alkylisourea is brought into contact with nitric acid in the presence of concentrated sulfuric acid or fuming sulfuric acid. In the mixing of 5-(aminomethyl)-2-chlorothiazole with the compound (3), there is no limitation on the amount of the compound (3). The amount is usually from 0.2 to 5 mol, and preferably from 0.7 to 1.5 mol, based on 1 mol of 5-(aminomethyl)-2-chlorothiazole. The above mixing may be carried out in the absence of any solvent, and is usually carried out in a solvent, such as water or an organic solvent. The mixing can be usually carried out at a temperature of 0 to 80° C., and preferably of 5 to 50° C. The above mixing can be usually carried out at pH 5 to 9, and preferably at pH 6 to 8.

Also, the compound (1) can be obtained by denitramidation of the compound (4). The denitramidation can be carried out by bringing the compound (4) into contact with ammonia.

The denitramidation is preferably carried out in an organic solvent. Examples of the organic solvent include nitrile solvents, such as acetonitrile and ether solvents, such as tetrahydrofuran. The contact of the compound (4) with ammonia is preferably carried out by dissolving the compound (4) in the organic solvent and then adding ammonia water dropwise to the obtained solution.

In the denitramidation, ammonia is preferably brought into contact in the amount of 2 to 10 mol based on 1 mol of the compound (4). In the denitramidation, preferred temperature is from 0 to 40° C. and preferred pressure is from 90 kPa to atmospheric pressure.

EXAMPLES

The present invention will be described in more detail below by way of Examples. Percentages are by weight unless otherwise specified.

Reference Example 1

Production Example of Compound (1)

While stirring N-(2-chlorothiazol-5-ylmethyl)-O-methyl-N'-nitroisourea (50 g) in acetonitrile (400 mL), 28% ammonium water (58.6 g) was added dropwise to the mixture at 25 to 30° C. The obtained mixture was maintained at the same temperature for 1 hour, and then acetonitrile was distilled off under reduced pressure.

The obtained residue was diluted with ethyl acetate (120 mL) and the solution was dehydrated over anhydrous magnesium sulfate (5 g), and then insoluble components were filtered off from the obtained mixture and the obtained solution was concentrated under reduced pressure. The obtained oily substance was dissolved by adding toluene (50 mL) and n-hexane (30 mL), and a crystal was precipitated by gradually adding n-hexane.

The crystal was collected by filtration and then recrystallized by adding toluene and n-hexane in the same manner as described above. The obtained crystal was collected by filtration and dried under reduced pressure to obtain 18 g of a white crystal of N-(2-chlorothiazol-5-ylmethyl)-O-methylisourea.

Purity based on area percentage in high-performance liquid chromatography: 98.3%

Melting point: 71 to 72° C.

$^1$H-NMR: 3.7 (s, 3H), 4.4 (s, 2H), 4.9 (s, 2H), 7.4 (s, 1H)

Reference Example 2

Production Example of Compound (3)

O-Methylisourea ½ sulfate salt (65 g, content: 98%, 0.5 mol) was dissolved in fuming sulfuric acid (100 g, concentration of sulfur trioxide: 10% by weight), and 98% nitric acid (82 g, 1.3 mol) was added dropwise to the obtained mixture at 10° C. over 1 hour. After the addition, the mixture was stirred at the same temperature for 6 hours to obtain a solution (236 g) containing O-methyl-N-nitroisourea.

Analysis by high-performance liquid chromatography revealed that the reaction solution contained 23% by weight of O-methyl-N-nitroisourea.

Reference Example 3

Production Example of Compound (4)

The solution (236 g) containing O-methyl-N-nitroisourea was added dropwise to water (170 g) with stirring at 10° C. or lower. The solution was neutralized to pH 7 to 8 by adding an aqueous 27% by weight solution (490 g) of sodium hydroxide at 20° C. or lower.

To the neutralized mixture, an aqueous solution (211 g) of 5-(aminomethyl)-2-chlorothiazole hydrochloride (content: 34.6% by weight) was added. Then, an aqueous 5% solution of sodium hydroxide was added to adjust the pH of the obtained mixture to pH 6.5 to 7. The obtained solution was stirred at 20° C. for 14 hours. The temperature was then raised up to 30° C. and the solution was further stirred for 12 hours to obtain a mixture containing a crystal. During stirring, the pH of the mixture was maintained at pH 6.5 to 7 with an aqueous 5% solution of sodium hydroxide.

The mixture was filtered and the obtained crystal was washed with warm water, and then the filtrate and wash solution were combined to recover a solution (1,500 g). The recovered solution contained N-(2-chlorothiazol-5-ylmethyl)-O-methylisourea at a concentration of 1.4% by weight.

On the other hand, the obtained crystal was dried under reduced pressure to obtain 71 g of N-(2-chlorothiazol-5-ylmethyl)-O-methyl-N'-nitroisourea.

Example 1-1

To a solution (3,000 g) containing 1.5% by weight of N-(2-chlorothiazol-5-ylmethyl)-O-methyl-isourea obtained in the same manner as in Reference Example 3, an aqueous 27% by weight solution (150 g) of sodium hydroxide was added, and the mixture was heated to 80° C. and maintained at the same temperature for 3 hours. Subsequently, the obtained mixture was cooled to room temperature (about 20° C.) to obtain a crystal containing N-(2-chlorothiazol-5-ylmethyl)-urea. The crystal was filtered, washed with water, and dried under reduced pressure to obtain 36 g of a crystal.

The content of N-(2-chlorothiazol-5-ylmethyl)-urea in the crystal was 93% by weight, and the yield from N-(2-chlorothiazol-5-ylmethyl)-O-methyl-N'-isourea was 75%.

Example 1-2

N-(2-Chlorothiazol-5-ylmethyl)-O-methyl-N'-isourea (150 g, content: 93% by weight) obtained in the same manner as in Example 1-1 was dissolved in 30% sulfuric acid (1330 g) at 40° C.

To the obtained sulfuric acid solution, an aqueous 30% by weight solution (245 g) of sodium nitrite was added dropwise at the same temperature over 2 hours. The obtained mixture was further stirred at the same temperature over 1 hour, and the obtained reaction solution was cooled to room temperature. To the solution, a 27% by weight aqueous solution (1290 g) of sodium hydroxide was added to adjust the pH to pH 13, and the solution was extracted twice with toluene (750 g).

Water (140 g) and 35% by weight concentrated hydrochloric acid (67 g) were added to a combined toluene layer, and then the toluene layer was separated to obtain an aqueous solution (315 g) of 5-(aminomethyl)-2-chlorothiazole hydrochloride.

Analysis of the aqueous solution by high-performance liquid chromatography revealed that the content of 5-(aminomethyl)-2-chlorothiazole was 36.5% by weight, and the yield from N-(2-chlorothiazol-5-ylmethyl)-urea was 85%.

Example 2

A solution containing 1.5% by weight of N-(2-chlorothiazol-5-ylmethyl)-O-methylisourea was obtained in the same manner as in Reference Example 3. To the solution (1000 g), a 27% by weight aqueous solution (50 g) of sodium hydroxide and diatomaceous earth (Radiolite #700, 5 g) were added, and the obtained mixture was heated to 80° C. and maintained at the same temperature for 3 hours. Subsequently, insoluble components were filtered off at the same temperature.

The filtrate was cooled to room temperature to obtain a crystal containing N-(2-chlorothiazol-5-ylmethyl)-urea. The crystal was filtered, washed with water and then dried under reduced pressure to obtain 36 g of a crystal.

The content of N-(2-chlorothiazol-5-ylmethyl)-urea in the crystal was 93% by weight, and the yield from N-(2-chlorothiazol-5-ylmethyl)-O-methyl-N'-isourea was 69%.

Example 3

A solution containing 1.5% by weight of N-(2-chlorothiazol-5-ylmethyl)-O-methyl-isourea was obtained in the same manner as in Reference Example 3. To the solution (800 g), a 27% by weight aqueous solution (40 g) of sodium hydroxide was added, and the mixture was heated to 80° C. and maintained at the same temperature for 3 hours.

Toluene (80 g) was added at the same temperature and the mixture was stirred. Subsequently, the mixture was separated into a toluene layer and an aqueous layer. The obtained aqueous layer was cooled to room temperature (about 20° C.) to obtain a crystal containing N-(2-chlorothiazol-5-ylmethyl)-urea. The crystal was filtered, washed with water and then dried under reduced pressure to obtain 9.1 g of a crystal.

The content of N-(2-chlorothiazol-5-ylmethyl)-urea in the crystal was 97% by weight, and the yield from N-(2-chlorothiazol-5-ylmethyl)-O-methyl-N'-isourea was 72%.

INDUSTRIAL APPLICABILITY

The present invention can provide a method for producing 5-(aminomethyl)-2-chlorothiazole.

The invention claimed is:

1. A method for producing 5-(aminomethyl)-2-chlorothiazole, which comprises the step of mixing a compound represented by formula (2):

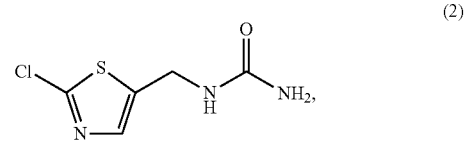 [SMILES: NC(=O)NCc1cnc(Cl)s1]

a mineral acid and a nitrite salt together.

2. The method according to claim 1, wherein the mineral acid is at least one selected from the group consisting of hydrochloric acid, sulfuric acid and phosphoric acid.

3. A method for producing a compound represented by formula (2):

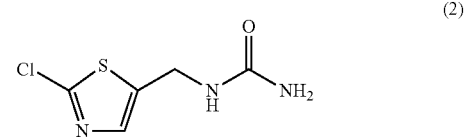 [SMILES: NC(=O)NCc1cnc(Cl)s1]

which comprises the step of hydrolyzing a compound represented by formula (1):

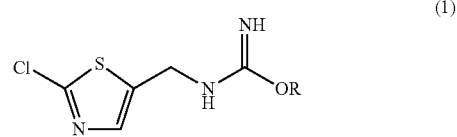

wherein R represents a linear alkyl group having 1 to 6 carbon atoms or a cyclic alkyl group having 3 to 6 carbon atoms, and each of the linear alkyl group and the cyclic alkyl group may have a substituent.

4. A method for producing 5-(aminomethyl)-2-chlorothiazole, which comprises the steps of:

hydrolyzing a compound represented by formula (1):

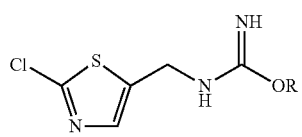
(1)

wherein R represents a linear alkyl group having 1 to 6 carbon atoms or a cyclic alkyl group having 3 to 6 carbon atoms, and each of the linear alkyl group and the cyclic alkyl group may have a substituent, and mixing an N-carbamoylamino compound obtained in the above step and represented by formula (2):

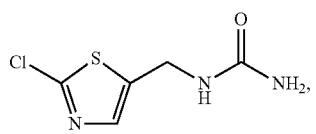
(2)

a mineral acid and a nitrite salt together.

5. The method according to claim 4, wherein the mineral acid is at least one selected from the group consisting of hydrochloric acid, sulfuric acid and phosphoric acid.

6. The method according to claim 4, wherein the compound represented by formula (1) is a compound contained in a solution obtained by mixing 5-(aminomethyl)-2-chlorothiazole with a compound represented by formula (3):

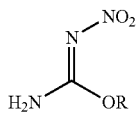
(3)

wherein R has the same meaning as defined in claim 4, in the presence of a solvent to obtain a mixture containing a compound represented by formula (4):

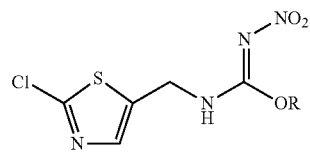
(4)

wherein R has the same meaning as defined above, and the compound represented by formula (1), and then subjecting the mixture to solid-liquid separation.

7. The method according to claim 6, wherein the solvent is water or a mixed solvent of water and an organic solvent.

8. A method for producing a compound represented by formula (4):

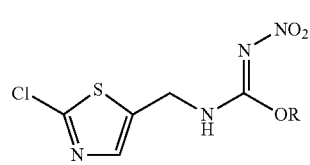
(4)

wherein R is as defined in claim 4, which comprises the step of mixing 5-(aminomethyl)-2-chlorothiazole obtained by the method according to claim 4 with a compound represented by formula (3):

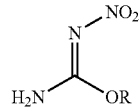
(3)

wherein R has the same meaning as defined above.

* * * * *